United States Patent [19] … [11] Patent Number: 4,640,702
Grabiak et al. … [45] Date of Patent: Feb. 3, 1987

[54] 2-CHLORO-4-TRIFLUOROMETHYL-THIAZOLECARBOTHIOIC ACIDS USEFUL AS HERBICIDAL SAFENERS

[75] Inventors: Raymond C. Grabiak, Creve Coeur; Robert K. Howe, Bridgeton; David E. Schafer, Olivette, all of Mo.

[73] Assignee: Monsanto Company, St. Louis, Mo.

[21] Appl. No.: 168,959

[22] Filed: Jul. 14, 1980

[51] Int. Cl.$^4$ ............... A01N 43/78; C07D 277/34
[52] U.S. Cl. ............................. 71/90; 71/118; 548/201; 47/57.6
[58] Field of Search ............... 71/90, 118; 548/201, 548/200; 47/57.6

[56] References Cited

U.S. PATENT DOCUMENTS

| | | | |
|---|---|---|---|
| 2,139,570 | 12/1938 | Andersag et al. | 260/302 |
| 2,726,237 | 12/1955 | Towne et al. | 260/158 |
| 2,726,247 | 12/1955 | Towne et al. | 260/306.8 |
| 3,536,727 | 10/1970 | Cavalla et al. | 260/302 |
| 3,833,601 | 9/1974 | Beck et al. | 260/302 R |
| 4,199,506 | 4/1980 | Howe et al. | 548/201 |
| 4,317,310 | 3/1982 | Bollinger | 47/57.6 |

OTHER PUBLICATIONS

M. Wohmann, CZ 1891 #1, pp. 68–69, "Die Diazoverbindungen der Thiazolreihe and ihre Reactionen".
Clarke et al, J. Chem. Soc. (B), 1966, pp. 339, 341–343, "Studies in Mass Spectrometry, Part VII, Mass Spectra of Thiazoles".

*Primary Examiner*—Catherine L. Mills
*Attorney, Agent, or Firm*—J. Timothy Keane

[57] ABSTRACT

2-chloro-4-trifluoromethyl-5-thiazolecarbothioic acid derivatives having the formula

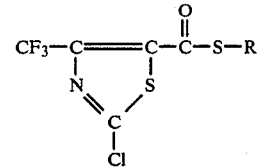

where R is $C_{1-5}$ alkyl, phenyl or benzyl, have been found to be effective in reducing herbicidal injury to grain sorghum caused by the application thereto of a 2-haloacetanilide herbicide, especially, alachlor.

34 Claims, No Drawings

2-CHLORO-4-TRIFLUOROMETHYL-THIAZOLECARBOTHIOIC ACIDS USEFUL AS HERBICIDAL SAFENERS

This invention relates to novel 2-chloro-4-trifluoromethyl-5-thiazolecarbothioic acid derivatives which are useful in compositions and methods for reducing herbicidal injury. More specifically, the invention relates to novel compositions and methods for reducing injury to crop plants by 2-haloacetanilide herbicides, especially, 2-chloro-2',6'-diethyl-N-(methoxymethyl) acetanilide (hereinafter referred to as alachlor), which comprises treating the crop plant or the seed of the crop plant with an effective amount of a 2-chloro-4-trifluoromethyl-5-thiazolecarbothioic acid compound, described more fully below.

BACKGROUND OF THE INVENTION

2-Haloacetanilide herbicides, especially alachlor, are very useful for controlling weeds in the presence of growing crops, especially sorghum. Application of these herbicides to crop plants at rates necessary to kill or stunt weeds, however, may injure the crop plant slowing growth and development. Accordingly, a safening agent consisting of a chemical compound that could be used to treat either the seed of the crop plant, the crop plant locus, or the crop plant itself, such that a reduction of injury due to application of the herbicide without a corresponding reduction of herbicidal action on the weed, would be quite beneficial.

DESCRIPTION OF THE INVENTION

In accordance with the novel aspects of the present invention, injury to grain sorghum or corn, especially sorghum, due to application thereto of 2-haloacetanilide herbicides, may be reduced without a corresponding reduction in injury to the weeds by application to the crop plant, the crop plant locus or the seed of the crop plant prior to planting, of an effective amount of a safening agent comprising a 2-chloro-4-trifluoromethyl-5-thiazolecarbothioic acid derivative having the formula

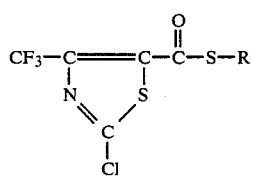

(I)

wherein R is $C_{1-5}$ alkyl, phenyl or benzyl.

The following may be mentioned as examples of the 2-chloro-4-trifluoromethyl-5-thiazolecarbothioic acid derivatives which are useful as herbicidal safeners in the methods and compositions of this invention: Phenyl 2-chloro-4-trifluoromethyl-5-thiazolecarbothioate, benzyl 2-chloro-4-trifluoro-methyl-5-thiazolecarbothioate, ethyl 2-chloro-4-trifluoromethyl-5-thiazolecarbothioate, methyl 2-chloro-4-trifluoromethyl-5-thiazolecarbothioate, isopropyl 2-chloro-4-trifluoromethyl-5-thiazolecarbothioate, n-propyl 2-chloro-4-trifluoromethyl-5-thiazolecarbothioate, n-butyl 2-chloro-4-trifluoromethyl-5-thiazolecarbothioate, tert-butyl 2-chloro-4-trifluoromethyl-5-thiazolecarbothioate, sec-butyl 2-chloro-4-trifluoromethyl-5-thiazolecarbothioate, isobutyl 2-chloro-4-trifluoromethyl-5-thiazolecarbothioate, and n-pentyl 2-chloro-4-trifluoromethyl-5-thiazolecarbothioate.

Compounds of the present invention may be prepared according to the following scheme:

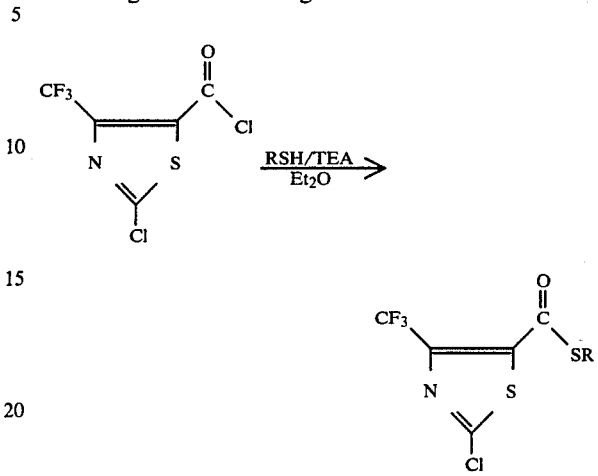

where R is as defined in Formula I. In accordance with the above reaction scheme, 2-chloro-4-trifluoromethyl-5-thiazolecarbonyl chloride in anhydrous ether is added dropwise to from about 1 to about 2 equivalents of thiophenol. The preferred procedure for preparing these 5-thiazolecarbothioates employs 1.1 equivalents of the thiol for every equivalent of the thiazole. The use of excess thiol in this procedure may yield mixtures of the desired 2-chloro-substituted product as well as an —SR substituent group on the 2-position. The reaction mixture is held at ambient temperature for a number of hours, preferably one or two and the mixture is diluted with water and the layers separated. The ether layer is washed with 10% base (e.g., NaOH or KOH) and then with water. The dried ($MgSO_4$) ether solution is concentrated in vacuo to give the desired 5-thiazolecarbothioic acid esters.

Further details of the compounds of the present invention and their preparation are found in the following non-limiting examples.

EXAMPLE 1

Preparation of Phenyl 2-Chloro-4-Trifluoromethyl-5-Thiazolecarbothioate.

A magnetically stirred mixture of 2-chloro-4-trifluoromethyl-5-thiazolecarboxylic acid in an excess of thionyl chloride was heated at reflux for 3–5 hours. The excess thionyl chloride was removed in vacuo on a rotary evaporator to yield the crude acid chloride as a yellow oil. This oil was used immediately without further purification. 2.31 g (10 mmol) of 2-chloro-4-trifluoromethyl-5-thiazolecarbonyl chloride in 25 ml of anhydrous ether was added dropwise to a stirred mixture of thiophenol (2.2 g, 20 mmol) and triethylamine (1.5 g, 15 mmol) in 100 ml of anhydrous ether at room temperature. After being stirred an additional hour at ambient temperature, the mixture was diluted with $H_2O$ and the layers separated. The ether layer was washed with 10% NaOH and then with $H_2O$. The dried ($MgSO_4$) ether solution was concentrated in vacuo to yield a beige solid; 2.9 g. This solid was recrystallized from hexane to yield white, feathery needles identified as phenyl 2-chloro-4-trifluoromethyl-5-thiazolecarbothioate; 0.9 g (25% yield), mp 115°–117° C.

Anal. Calc'd for $C_{17}H_{10}F_3NOS_3$: C, 51.37; H, 2.54; N, 3.52; S, 24.20. Found: C, 51.21; H, 2.39; N, 3.51; S, 23.75.

EXAMPLE 2

Preparation of Benzyl 2-Chloro-4-Trifluoromethyl-5-Thiazolecarbothioate.

2-Chloro-4-trifluoromethyl-5-thiazolecarbonyl chloride, (2.31 g, 10 mmol) in 50 ml of anhydrous ether was added dropwise to a stirred mixture of benzyl mercaptan (1.36 g, 11 mmol) and triethylamine (1.5 g, 15 mmol) in 75 ml of anhydrous ether at ambient temperature over a period of 20 minutes. The resulting mixture was stirred for an additional hour, diluted with $H_2O$ and the layers separated. The ether layer was washed with 10% NaOH and then with $H_2O$. The dried ($MgSO_4$) ether solution was concentrated in vacuo to yield a yellow solid; 3 g. Recrystallization from hexane at $-72°$ C. yielded benzyl 2-chloro-4-trifluoromethyl-5-thiazolecarbothioate as yellow needles; 2.55 g (75% yield); mp 61°–63° C.

Anal. Calc'd for $C_{12}H_7ClF_3NOS_2$: C, 42.67; H, 2.09; Cl, 10.50; N, 4.15; S, 18.99. Found: C, 42.97; H, 2.16; Cl, 10.72; N, 4.14; S, 18.81.

EXAMPLE 3

Preparation of Ethyl 2-Chloro-4-Trifluoromethyl-5-Thiazolecarbothioate.

5.95 g (25.7 mmol) of 2-chloro-4-trifluoromethyl-5-thiazolecarbonyl chloride in 50 ml of anhydrous ether was added dropwise at 0° C. to a mechanically stirred mixture of ethyl mercaptan (2.1 ml, 28.3 mmol) and triethylamine (3 g, 30 mmol) in 100 ml of anhydrous ether. The workup for this reaction was the same as Example 1 except that the crude pale yellow oil was distilled in a Kugelrohr at 80° C./0.55 mm to yield a colorless oil, 5.59 g. This oil was crystallized from petroleum ether at $-72°$ C. to yield ethyl 2-chloro-4-trifluoromethyl-5-thiazolecarbothioate as a white solid; 4.8 g (68% yield), mp 28°–32° C.

Anal. Calc'd for $C_7H_5ClF_3NOS_2$: C, 30.50; H, 1.83; Cl, 12.86; N, 5.08; S, 23.26. Found: C, 30.59; H, 1.91; Cl, 12.62; N, 4.95; S, 23.58.

The 2-chloro-4-trifluoro-methyl-5-thiazolecarbothioic acid esters may be used to protect crop plants from the herbicidal action of 2-haloacetanilide herbicides, without a corresponding diminution in herbicidal activity to the weeds. 2-Haloacetanilide herbicides specifically contemplated for use in the method of this invention are 2-chloro-2',6'-diethyl-N-(methoxymethyl) acetanilide (alachlor), 2'-methoxy-6'-methyl-N-(isopropoxy) methyl-2-chloroacetanilide, isopentoxy-6'-methyl-N-methyl-2-chloroacetanilide and -2-n-butoxy-6'-methyl-N-methyl-2-n-butoxy-6'-methyl-N-methyl-2-chloroacetanilide; these compounds are disclosed in Ser. No. 133,695, filed Mar. 25, 1980, and Ser. No. 133,758, filed Mar. 25, 1980. The amount of safening agent employed in the methods and compositions of the invention will vary depending upon the manner of application, rate of application, environmental factors as well as other factors known in the art. In each instance, the amount employed is a safening effective amount, i.e., the amount which reduces crop injury by the herbicide. The amount of herbicide employed in the method and compositions of the invention is a "herbicidally effective amount", i.e., rates which produce effective controls of undesirable vegetation.

The safening agent may be applied to the plant locus in a mixture with the herbicide, sequentially, i.e., the safening agent may be applied before or after the herbicide or it may be applied directly to the crop seed itself. By application to the "plant locus" is meant application to the plant growing medium, such as the soil, as well as the seeds, emerging seedlings, roots, stems, leaves, flowers, fruits or other plant parts.

One preferred embodiment of the present invention is directed to the use of the safening compounds described herein in a method of safening sorghum against the herbicidal action of alachlor herbicide. Yet another preferred embodiment is directed to the use of the safening compounds described herein in a method of safening corn against the herbicidal action of 2'-methoxy-6'-methyl-N-(isopropoxy) methyl-2-chloroacetanilide, isopentoxy-6'-methyl-N-methyl-2-chloroacetanilide and -2-n-butoxy-6'-methyl-N-methyl-2-n-butoxy-6'-methyl-N-methyl-2-chloroacetanilide.

To illustrate the effectiveness of the 2-chloro-4-trifluoromethyl-5-thiazolecarbothioic acid ester compounds, the following examples are presented. These examples are presented merely as being illustrative of the novel aspects of the invention and are not intended to be a limitation as to the scope thereof.

EXAMPLE 4

A good grade of top soil is placed in a container and compacted to a depth of approximately 1.27 cm. from the top of said container. A predetermined number of sorghum seeds are placed on top of the soil. A quantity of soil sufficient to substantially fill the container is measured and placed in a second container. A measured quantity of the safening agent dispersed or dissolved in a suitable carrier is applied to the soil in the second container. A measured quantity of alachlor herbicide dispersed or dissolved in a suitable carrier is then sprayed on the soil already treated with the safening agent. The soil containing the safening agent and herbicide is thoroughly mixed. This mixing is sometimes referred to as incorporation of the herbicide and safening agent into the soil. The mixing or incorporation provides a substantially uniform distribution of the safening agent and herbicide throughout the soil. The seeds are covered with the soil containing the safening agent and alachlor herbicide and the pots are leveled. The pots are then placed on a sand bench in the greenhouse and watered from below as needed. The plants are observed at the end of approximately 21 days and the results in terms of percent inhibition of each seed lot are recorded. For each test series, a pot is also prepared containing no alachlor herbicide and no safening agent as a control. Additionally, for each series of tests, the herbicidal effect of the alachlor herbicide is observed from pots treated with the same quantity of herbicide alone. The "safening effect" is determined by subtracting the herbicidal effect obtained when both the herbicide and safening agent are incorporated into the soil as discussed above, from the herbicidal effect observed when alachlor only was applied, i.e., the "Safening effect" is equal to:

| % Inhibition Due to Herbicide Only | — | % Inhibition due to Combination of Herbicide and Safening Agent. |
|---|---|---|

Table I summarizes the results obtained when the compounds of the invention were tested on sorghum plants in accordance with the procedure of Example 4 utilizing alachlor as the herbicide.

TABLE I

| Safening Agent Compound of Example No. | Rate of Safening Agent (kg/h) | Rate of Alachlor Herbicide (kg/h) | Safening Effect |
| --- | --- | --- | --- |
| 1 | 8.96 | 2.24 | 45 |
| 2 | 8.96 | 2.24 | 23 |
| 3 | 8.96 | 2.24 | 23 |

The 2-chloro-4-trifluoromethyl-5-thiazolecarbothioates of this invention may be used to protect crops from the herbicidal activity of 2-haloacetanilide herbicides, especially alachlor, without a corresponding diminution in herbicidal activity to the weeds. Example 5 is illustrative of such activity.

EXAMPLE 5

A good grade of top soil was placed in a plastic pot and compacted to a depth of approximately 1.27 cm. from the top of said pot. A predetermined number of crop seeds and weed seeds were placed on top of the soil. A soil cover layer, approximately 1.27 cm., was placed on top of said seeds. The soil was then treated with a mixture of the safening agent and alachlor dispersed or dissolved in a suitable solvent. For each test series, pots were treated with only the herbicide. Additionally, pots were treated with only the safening agent. The herbicidal effect was observed approximately 21 days after treatment. In this example "Safening Effect" is calculated as follows:

| % Inhibition Due to Herbicide Only | — | % Inhibition due to Combination of Herbicide and Safening Agent. |
| --- | --- | --- |

Table II summarizes the results obtained when several of the compounds of the invention were tested in accordance with the procedure of Example 5.

TABLE II

| Rate of Alachlor Herbicide (kg/h) | Safening Agent Compound of Example No. | Rate of Safening Agent (kg/h) | % Inhibition Green Foxtail | % Inhibition Sorghum | Safening Effect- Sorghum |
| --- | --- | --- | --- | --- | --- |
| 0.56 | — | — | 95 | 70 | — |
| 1.12 | | | 98 | 80 | — |
| 2.24 | | | 98 | 85 | — |
| 4.48 | | | 99 | 90 | — |
| — | 1 | 8.96 | 0 | 0 | — |
| 0.56 | | " | 98 | 0– | 70 |
| 1.12 | | " | 98 | 10– | 70 |
| 2.24 | | " | 99 | 10– | 75 |
| 4.48 | | " | 99 | 25– | 65 |
| — | 2 | " | 0 | 0 | — |
| 0.56 | | " | 98 | 0– | 70 |
| 1.12 | | " | 98 | 10– | 70 |
| 2.24 | | " | 98 | 20– | 65 |
| 4.48 | | " | 100 | 25– | 65 |
| — | 3 | " | 0 | 0 | — |
| 0.56 | | " | 98 | 0– | 70 |
| 1.12 | | " | 98 | 10– | 70 |
| 2.24 | | " | 99 | 15– | 70 |
| 4.48 | | " | 100 | 30– | 60 |

–Denotes significant safening effect.

EXAMPLE 6

Several of the compounds of this invention dissolved in methylene chloride were applied as seed treatments to grain sorghum. Seed treatment rates were based on % weight of seed, e.g., 1/64% w/w indicates that 0.16 grams of safening agent was applied to 1000 grams of sorghum seed, 1/8% w/w indicates that 1.25 grams of safening agent was applied to 1000 grams of seed, etc. Both treated and untreated sorghum seeds were planted in 11.4×13.3×7.0 cm. deep pans containing Ray silt loam soil. Selected weed species were planted in separate pans. 1.27 cm. deep soil cover layers (450 gm) were placed on each pre-seeded pan. Alachlor was applied to the soil surface with the belt sprayer. The pans were given 0.6 cm. of overhead water, transferred to greenhouse benches and subirrigated as required for the duration of the test.

Table III summarizes the results obtained when several of the compounds of this invention were tested in accordance with Example 6.

TABLE III

| Rate of Alachlor Herbicide (kg/h) | Safening Agent Compound of Example No. | % Sorghum Inhibition Seed Treatment Conc. % w/w | | | |
| --- | --- | --- | --- | --- | --- |
| | | 0 | 1/64 | ⅛ | 1 |
| — | 1 | 0 | 0 | 0 | 0 |
| 0.28 | | 83 | 5– | 0– | 5– |
| 1.12 | | 98 | 20– | 5– | 10– |
| 4.48 | | 100 | 83 | 48– | 33– |
| — | 2 | 0 | 0 | 0 | 0 |
| 0.28 | | 60 | 8– | 0– | 10– |
| 1.12 | | 97 | 15– | 8– | 13– |
| 4.48 | | 100 | 85 | 50– | 63– |
| — | 3 | 0 | 0 | 0 | 15 |
| 0.28 | | 65 | 33– | 10– | 30– |
| 1.12 | | 90 | 73 | 35– | 35– |
| 4.48 | | 100 | 99 | 70– | 45– |

| | % Inhibition | | | | | | |
| --- | --- | --- | --- | --- | --- | --- | --- |
| | Sorghum | Barnyard-grass | Lambs-quarter | Green Foxtail | Smart-weed | Pani-cum | Crab-grass |
| — | 0 | 0 | 0 | 0 | 0 | 0 | 0 |
| 0.07 | 70 | 98 | 20 | 50 | 10 | 65 | 70 |
| 0.28 | 80 | 100 | 30 | 88 | 55 | 88 | 98 |
| 1.12 | 99 | 100 | 63 | 95 | 70 | 95 | 100 |
| 4.48 | 99 | 100 | 100 | 99 | 98 | 99 | 100 |

Example 7

A good grade of top soil was placed in a plastic pot (9.37×9.37×8.25 cm deep) and compacted to a depth of 1.28 cm from the top of the pot. The pots were then planted with seeds of the desired plant species. The safening agent dissolved in a suitable volume of solvent was pipetted onto the soil surface of pre-prepared cover layers. The soil layers treated with the safening agent were thereafter sprayed with the desired herbicide at the appropriate rate. After application of the herbicide the soil cover layer was stirred or shaken to incorporate the safening agent and herbicide. The soil cover layers were then placed in the pre-seeded plastic pots, which were then transferred to greenhouse benches and subirrigated for the duration of the test. Approximately 20 days after application of the safening agent and herbicide, the results were observed and recorded. In the test summarized in Table IV, the 2-haloacetanilide herbicides utilized were as follows:

A = 2'-methoxy-6'-methyl-N-(isopropoxymethyl)-2-chloroacetanilide,
B = 2'-isopentoxy-6'-methyl-N-methyl-2-chloroacetanilide, and
C = 2'-n-butoxy-6'-methyl-N-methyl-2-)chloroacetanilide.

The data is summarized in Table IV.

TABLE IV

| Herbicide | Rate of Herbicide (kg/ha) | Safening Agent Compound of Example No. | Rate of Safening Agent (kg/ha) | % Inhibition Sorghum | % Inhibition Field Corn |
|---|---|---|---|---|---|
| A | 1.12 | — | — | 98 | 95 |
| B | " | — | — | 100 | 95 |
| C | " | — | — | 100 | 98 |
| A | " | 1 | 8.96 | 50– | 10– |
| B | " | " | " | 100 | 45– |
| C | " | " | " | 100 | 60– |
| A | " | 2 | " | 20– | 30– |
| B | " | " | " | 100 | 70– |
| C | " | " | " | 100 | 80 |
| A | " | 3 | " | 20– | 25– |
| B | " | " | " | 100 | 45– |
| C | " | " | " | 100 | 75– |

–Denotes significant safening

The above examples illustrate that the 2-chloro-4-trifluoromethyl-5-thiazolecarbothioates of the present invention are useful in reducing 2-haloacetanilide herbicide injury to crop plants, especially in reducing alachlor injury to sorghum plants. The safening agent may be applied to the plant locus as a mixture, i.e., a mixture of a herbicidally effective amount of herbicide and a safening effective amount of safening agent, or sequentially, i.e., the plant locus may be treated with an effective amount of 2-haloacetanilide herbicide followed by a treatment with the safening agent or vice versa. The ratio of herbicide to safening agent may vary depending upon various factors, such as the weeds to be inhibited, mode of application, etc., but normally a herbicide to safening agent ratio ranging from 1:25 to 25:1 (preferably 1:5 to 5:1) parts by weight may be employed.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixtures thereof to the plant locus, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixtures thereof in a liquid or particulate solid form can be carried out by conventional techniques utilizing, for example, spreaders, power dusters, boom and hand sprayers, spray dusters and granular applicators. The compositions can also be applied from airplanes as a dust or spray. If desired, application of the compositions of the invention to plants can be accomplished by incorporating the compositions in the soil or other media.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

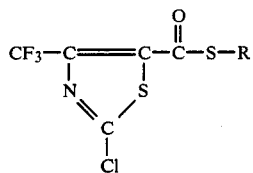

wherein R is $C_{1-5}$ alkyl, phenyl or benzyl.

2. A compound according to claim 1 wherein R is $C_{1-5}$ alkyl.

3. A compound according to claim 2 wherein R is ethyl.

4. A compound according to claim 2 wherein R is phenyl.

5. A compound according to claim 2 wherein R is benzyl.

6. A method of reducing herbicidal injury to sorghum plants due to application thereto of 2-haloacetanilide herbicides which comprises applying to the plant locus a non-phytotoxic, safening effective amount of a compound having the formula

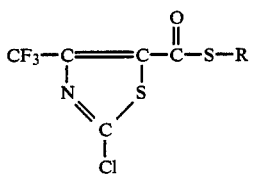

wherein R is $C_{1-5}$ alkyl, phenyl or benzyl.

7. A method according to claim 6 wherein R is $C_{1-5}$ alkyl.

8. A method according to claim 6 wherein R is ethyl.

9. A method according to claim 6 wherein R is phenyl.

10. A method according to claim 6 wherein R is benzyl.

11. A method according to claim 6 wherein said 2-haloacetanilide herbicide is alachlor.

12. A method according to claim 6 wherein said plant locus is the seed.

13. A method according to claim 6 wherein said plant locus is the soil.

14. A method of reducing herbicidal injury to corn plants due to application thereto of 2-haloacetanilide herbicides selected from the group consisting of 2'-methoxy-6'-methyl-N-(isopropoxymethyl)-2-chloroacetanilide; 2'-isopentoxy-6'-methyl-N-methyl-2-chloroacetanilide, and 2'-n-butoxy-6'-methyl-N-methyl-2-chloroacetanilide which comprises applying to the plant locus a non-phytotoxic, safening effective amount of a compound having the formula

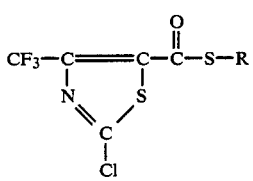

wherein R is $C_{1-5}$ alkyl, phenyl or benzyl.

15. A method according to claim 14 wherein R is $C_{1-5}$ alkyl.

16. A method according to claim 14 wherein R is ethyl.

17. A method according to claim 14 wherein R is phenyl.

18. A method according to claim 14 wherein R is benzyl.

19. A method according to claim 14 wherein said 2-haloacetanilide herbicide is alachlor.

20. A method according to claim 14 wherein said plant locus is the seed.

21. A method according to claim 14 wherein said plant locus is the soil.

22. A mixture which comprises a herbicidally effective amount of a 2-haloacetanilide herbicide selected from the group consisting of 2',6'-diethyl-N-(methoxymethyl)-2-chloroacetanilide, 2'-methoxy-6'-methyl-N-(isopropoxymethyl)-2-chloroacetanilide, 2'-isopentoxy-6'-methyl-N-methyl-2-chloroacetanilide and 2'-n-butoxy-6'-methyl-N-methyl-2-chloroacetanilide and a safening effective amount of a compound having the formula

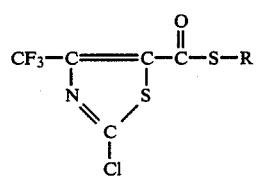

wherein R is $C_{1-5}$ alkyl, phenyl or benzyl.

23. A mixture according to claim 22 wherein R is $C_{1-5}$ alkyl.

24. A mixture according to claim 22 wherein R is ethyl.

25. A method according to claim 22 wherein R is phenyl.

26. A mixture according to claim 22 wherein R is benzyl.

27. A mixture according to claim 22 wherein said 2-haloacetanilide herbicide is alachlor.

28. A mixture according to claim 22 wherein the ratio of herbicide to safening agent is from about 1:25 parts by weight to about 25:1 parts by weight.

29. Seed, the plants grown from which are resistant to injury by 2-haloacetanilide herbicide, comprising crop seed coated with a safening effective amount of a compound having the formula

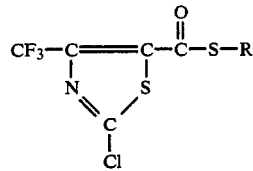

wherein R is $C_{1-5}$ alkyl, phenyl or benzyl.

30. Seed coated according to claim 29 wherein said herbicide is alachlor.

31. Seed coated according to claim 30 wherein said crop is sorghum.

32. Seed coated according to claim 29 wherein said herbicide is 2'-methoxy-6'-methyl-N-(isopropoxymethyl)-2-chloroacetanilide, 2'isopentoxy-6'-methyl-N-methyl-2-chloroacetanilide, and 2'-n-butoxy-6'-methyl-N-methyl-2-chloroacetanilide.

33. Seed coated according to claim 32 wherein said crop is corn.

34. Seed coated according to any of claims 29, 31 or 33 wherein said safening effective amount of compound is present at about 1.0 to about 10.0 parts of safening compound per 1000 parts of seed.

* * * * *